United States Patent [19]

Böger et al.

[11] Patent Number: 4,963,550
[45] Date of Patent: Oct. 16, 1990

[54] SUBSTITUTED THIOUREAS, ISOTHIOUREAS AND CARBODIIMIDES AND USE AS PESTICIDE

[75] Inventors: Manfred Böger, Weil am Rhein; Jozef Drabek, Oberwil; Josef Ehrenfreund, Allschwil; Odd Kristiansen, Möhlin, all of Switzerland

[73] Assignee: Ciba-Geigy Corporation, Ardsley, N.Y.

[21] Appl. No.: 476,200

[22] Filed: Feb. 7, 1990

Related U.S. Application Data

[62] Division of Ser. No. 84,652, Aug. 12, 1987, Pat. No. 4,914,099.

[30] Foreign Application Priority Data

Aug. 15, 1986 [CH] Switzerland ................... 3295/86

[51] Int. Cl.$^5$ .................. A01N 43/54; A01N 43/58; A01N 43/60; C07D 239/80
[52] U.S. Cl. ................................ 514/249; 514/248; 514/259; 544/237; 544/283; 544/285; 544/286; 544/287; 544/353; 544/354
[58] Field of Search ............... 544/237, 283, 285, 286, 544/287, 353, 354; 514/248, 249, 259

[56] References Cited

FOREIGN PATENT DOCUMENTS 00275965 6/1980 European Pat. Off. ............ 514/249
0177710 4/1986 European Pat. Off. ............ 514/249
2085878 10/1981 United Kingdom ............... 514/249

Primary Examiner—Mary C. Lee
Assistant Examiner—J. Richter
Attorney, Agent, or Firm—Kevin T. Mansfield; Edward McC. Roberts

[57] ABSTRACT

The invention relates to novel substituted N-phenylthioureas, N-phenylisothioureas and N-phenylcarbodiimides of formula

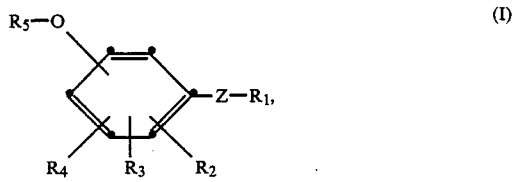

wherein $R_1$ to $R_5$ and Z are as defined in the specification.

The invention further relates to the preparation of said compounds and to compositions containing them for use in pest control, especially for controlling insects and representatives of the order Acarina that are pests of plants and animals, in particular plant-destructive sucking and eating pests.

15 Claims, No Drawings

SUBSTITUTED THIOUREAS, ISOTHIOUREAS AND CARBODIIMIDES AND USE AS PESTICIDE

This is a divisional of application Ser. No. 084,652 filed on Aug. 12, 1987, now U.S. Pat. No. 4,914,099.

The present invention relates to novel substituted N-phenylthioureas, N-phenylisothioureas and N-phenylcarbodiimides, to their preparation and to the use thereof in pest control.

The compounds of this invention have the formula I

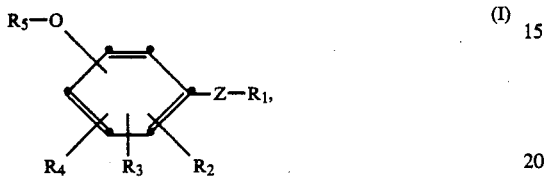

wherein
$R_1$ is $C_1$-$C_{12}$alkyl, $C_3$-$C_8$ cycloalkyl, polycyclic alkyl containing a total of 7 to 10 carbon atoms, $C_1$-$C_{12}$ alkyl which is substituted by 1 to 12 halogen atoms, $C_1$-$C_4$alkyl which is substituted by one or two $C_3$-$C_6$cycloalkyl radicals, alkoxyalkyl containing a total of 3 to 10 carbon atoms, $C_1$-$C_5$ alkyl which is substituted by a phenyl radical, $C_1$-$C_5$alkyl which is substituted by a phenyl radical which is in turn substituted by one or two members selected from the group consisting of halogen, methyl, methoxy and ethoxy; or is $C_3$-$C_{10}$alkenyl or $C_3$-$C_{10}$alkynyl,
$R_2$ is hydrogen or $C_1$-$C_4$alkyl,
$R_3$ is $C_1$-$C_4$alkyl
$R_4$ is hydrogen or $C_1$-$C_4$alkyl, and
$R_5$ is a radical selected from

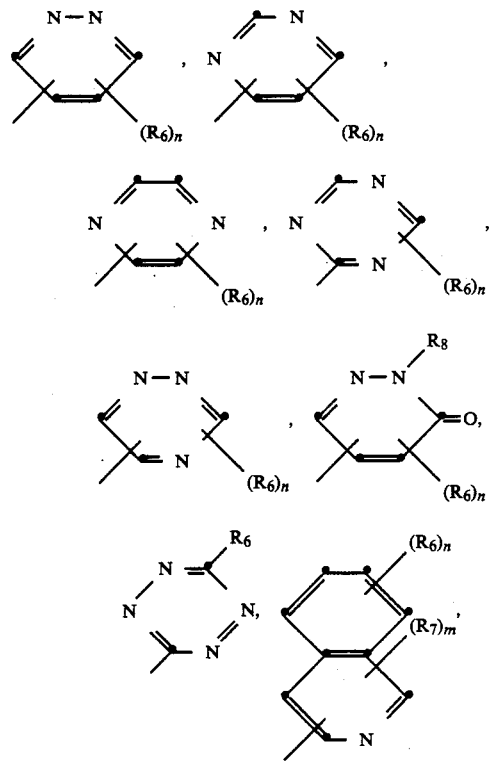

-continued

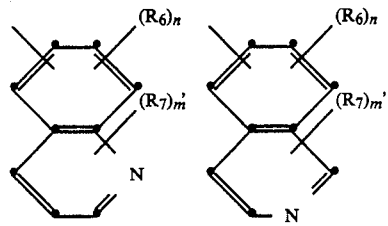

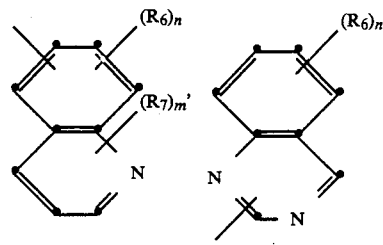

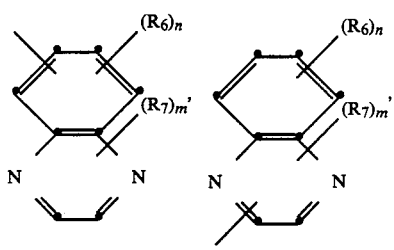

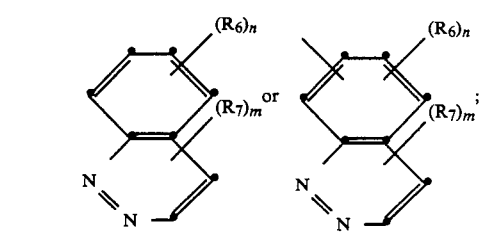

$R_6$ and $R_7$ are each independently of the other halogen, $C_1$-$C_4$alkyl, $C_1$-$C_3$alkyl which is substituted by 1 to 7 halogen atoms, $C_1$-$C_4$alkoxy, $C_1$-$C_3$alkoxy which is substituted by 1 to 7 carbon atoms; or is phenyl,
$R_8$ is $C_1$-$C_4$alkyl,
$R_9$ is $C_1$-$C_4$alkyl or $C_3$-$C_4$alkenyl,
n is an integer from 0 to 3,
m is an integer from 0 to 2, and
Z is a group selected from

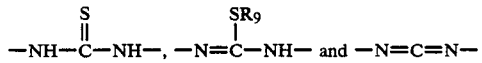

and the salts thereof.

The unsubstituted or substituted alkyl groups and substituents $R_1$ to $R_4$ and $R_9$ may be straight chain or branched. Examples of such groups are accordingly: methyl, ethyl, propyl, isopropyl, n-butyl, iso-butyl, sec-butyl and tert-butyl, n-pentyl, n-hexyl, n-heptyl, n-octyl, n-nonyl, n-decyl and the isomers thereof.

Within the scope of the present invention, halogen is preferably F, Cl and Br, with F and Cl being most preferred.

On account of their pesticidal activity, preferred compounds are those of formula Ia

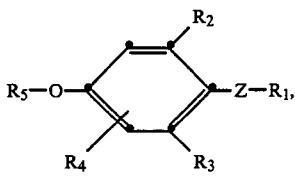

wherein the substituents R₁ to R₅ and Z are as defined above.

On account of their biological activity, useful compounds of formula I are also those wherein R₄ is hydrogen and those wherein Z is the group

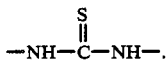

Compounds of formula I meriting particular attention on account of their good pesticidal activity are those wherein Z is the group

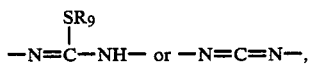

i.e. the isothioureas and carbodiimides.

Preferred compounds of formula I are those wherein R₅ is a radical selected from the group consisting of

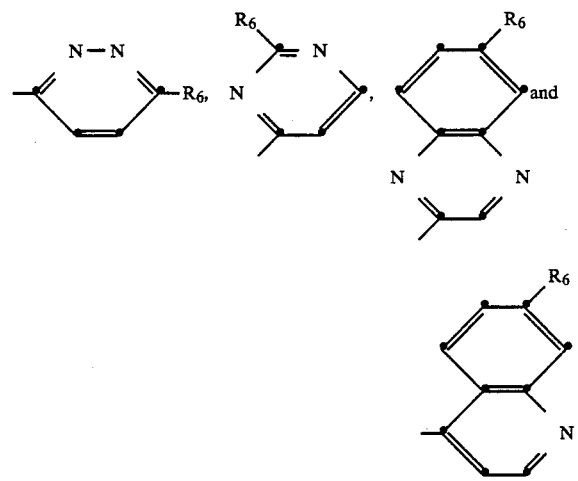

wherein R₆ is halogen or trifluoromethyl.

Further preferred compounds of formula I are those wherein R₁ is C₃-C₅alkyl, R₂ and R₃ are each independently of the other C₁-C₃alkyl and R₉ is methyl or ethyl; and also those wherein R₁ is isopropyl or tert-butyl, R₂ and R₃ are methyl or ethyl, R₄ is hydrogen and R₅ is methyl.

The compounds of formula I can be obtained in the form of addition salts or inorganic or organic acids and can also be used in the practice of this invention in the form of their salts. Accordingly, compounds of formula I will be understood as meaning within the scope of this invention the free compounds of formulae I and Ia as well as the acid addition salts thereof.

The compound of formula I can be converted into their acid addition salts by methods which are known per se. Examples of acids suitable for forming acid addition salts are: hydrochloric acid, hydrobromic acid, hydriodic acid, nitric acid, phosphoric acid, sulfuric acid, acetic acid, propionic acid, butyric acid, valeric acid, oxalic acid, malonic acid, succinic acid, malic acid, maleic acid, fumaric acid, lactic acid, tartaric acid, citric acid, benzoic acid, phthalic acid, cinnamic acid, phenylsulfonic acid and salicylic acid.

The compounds of formula I can be prepared by methods which are known per se (q.v. for example European patent application Nos. 0,175,649, 0,008,435 and DE-OS No. 2,730,620).

(A) A thiourea of formula I, wherein Z is the group

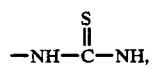

can be obtained e.g. by reacting a compound of formula II

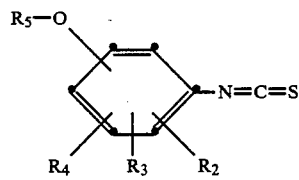

with a compound of formula III

in which formulae above the substituents R₁ to R₆ and n are as defined in claim 1.

The above process can preferably be carried out under normal pressure and in the presence of a preferably aprotic organic solvent or diluent. Examples of suitable solvents or diluents are: ethers and ethereal compounds such as diethyl ether, dipropyl ether, dibutyl ether, dioxane, dimethoxyethane and tetrahydrofuran; N,N-dialkylated carboxamides; aliphatic, aromatic and halogenated hydrocarbons, especially benzene, toluene, xylene, chloroform, methylene chloride, carbon tetrachloride and chlorobenzene; nitriles such as acetonitrile or propionitrile; and ketones, e.g. acetone, methyl ethyl ketone, methyl isopropyl ketone and methyl isobutyl ketone. The process is generally carried out at a temperature in the range from 0° to 150° C., preferably from 10° to 70° C., most preferably at room temperature.

The isothiocyanates of formula II can be obtained by thiophosgenating the appropriate anilines of formula V

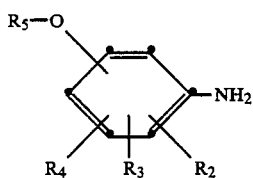

These anilines of formula V can be obtained e.g. by etherification as follows:

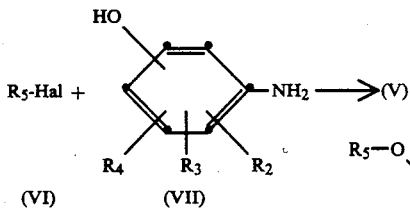

(VI)  (VII)

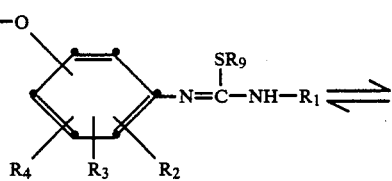

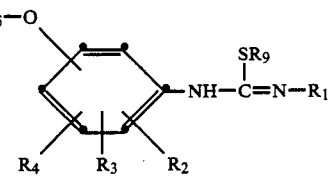

or

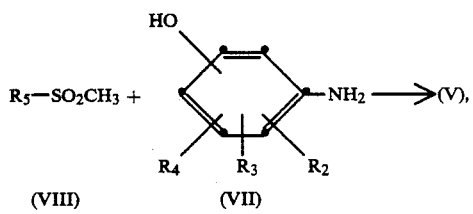

(VIII)  (VII), in which formulae V, VI, VII and VIII the substituents $R_2$ to $R_5$ are as defined above. The compounds of formulae VI and VIII as well as the hydroxyanilines of formula VII are known and can be prepared by conventional methods. The etherified anilines of formula V and the isothiocyanates of formula II are novel compounds and likewise fall within the scope of this invention.

(b) An isothioureas of formula I, wherein Z is the group

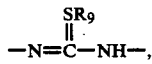

can be obtained by reacting a thiourea of formula I, wherein Z is the group

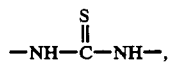

with a compound of formula IV

  (IV)

wherein $R_9$ is as defined for formula I and X is a leaving group, e.g. halogen such as chlorine, or sulfate, or methylsulfonate. The free isothiourea can be isolated from the isothiuronium salt by treatment with a base, e.g. an aqueous alkali hydroxide.

The above process is conveniently carried out in the temperature range from 10° to 250° C., preferably from 70° to 200° C., under normal or slightly elevated pressure and preferably in the presence of a solvent or diluent which is inert to the reactants. Examples of suitable solvents or diluents are: ethers and ethereal compounds such as diethyl ether, diisopropyl ether, dioxane, and tetrahydrofuran; aromatic hydrocarbons such as benzene, toluene or xylenes; ketones such as acetone, methyl ethyl ketone and cyclohexanone; alcohols and dimethylformamide. It is preferred to carry out the reaction at the reflux temperature of the reaction mixture.

The isothioureas of this invention can be obtained in their tautomeric forms

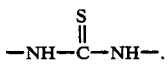

The invention encompasses both forms as such as well as mixtures of tautomers.

(C) A compound of formula I, wherein Z is the group —N=C=N—, i.e. a carbodiimide, can be prepared by eliminating hydrogen sulfide from a compound of formula I, wherein Z is the group $$-NH-\overset{\overset{S}{\|}}{C}-NH-.$$

Such elimination reactions can be carried out in accordance with procedures known from the literature, e.g. with the aid of HgO, specific pyridinium salts, chloroacetates, cyanuric chloride, p-toluenesulfochloride or specific phosphate derivatives [T. Shibanuma, Chemistry Letters (1977), pp. 575–576; S. Kim, Tetrahedron Letters (1985), pp. 1661–1664; W. Weith, B.6 (1873) 1398; G. Amiard, Bull. Soc. chim. 1956, 1360].

The above process can preferably be carried out under normal pressure and in the presence of a preferably aprotic organic solvent or diluent. Examples of suitable solvents or diluents are: ethers and ethereal compounds such as diethyl ether, dipropyl ether, dibutyl ether, dioxane, dimethoxyethane and tetrahydrofuran; N,N-dialkylated carboxamides; aliphatic, aromatic and halogenated hydrocarbons, especially benzene, toluene, xylene, chloroform, methylene chloride, carbon tetrachloride and chlorobenzene; nitriles such as acetonitrile or propionitrile; and ketones, e.g. acetone, methyl ethyl ketone, methyl isopropyl ketone and methyl isobutyl ketone. The process is generally carried out at a temperature in the range from $-0°$ to $+150°$ C., preferably from 10° to 50° C., e.g. at room temperature.

The carbodiimides falling under formula I can also be prepared in a manner known per se by reacting suitably substituted isocyanide dichlorides of formula III with a salt of the respective desired primary amine of formula IV (q.v. U.S. Pat. No. 3,231,610):

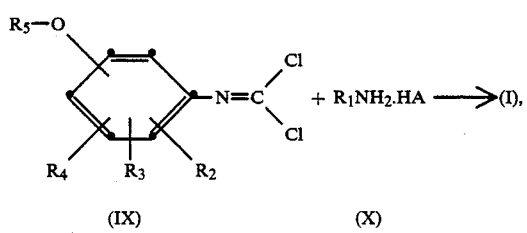

(IX)  (X)

in which formulae IX and X the radicals $R_1$ to $R_5$ are as defined above and A is an anion, e.g. $Cl^{\ominus}$.

Suitable primary amine salts for this reaction are e.g. the hydrohalides. The reaction is preferably carried out in the presence of an inert organic solvent with a relatively high boiling point, e.g. chlorinated benzenes, nitrobenzene, dimethylacetamide or tetramethylenesulfone. Examples of further suitable solvents are: high boiling aliphatic, cycloaliphatic and aromatic hydrocarbons such as p-chlorobromobenzene, 1-chloronaphthalene or halogenated xylenes. In general, the reaction is preferably carried out at a temperature in the range form 80° to 200° C.

The starting materials of formulae IX and X are known and, if novel, can be obtained in accordance with known procedures (q.v. Belgian patent specification No. 863 078, German patent application No. 1 094 737 and U.S. Pat. No. 3,932,507).

The compounds of formula I are particularly suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as representative of the order Acarina, in particular plant-destructive acarids, e.g. spider-mites.

The good pesticidal activity of the compounds of formula I of the invention corresponds to a mortality of at least 50–60 % of the above pests.

In addition to their very effective action against flies, e.g. *Musca domestica,* and mosquito larvae, the compounds of formula I are particularly suitable for controlling plant-destructive feeding insects in ornamentals and crops of useful plants, especially in cotton (e.g. against *Spodoptera littoralis* and *Heliothis virescens*) and in crops of vegetables (e.g. against *Leptinotarsa decemlineata* and *Pieris brassicae*). The larvicidal and ovicidal action of the compounds of formula I is to be particularly highlighted. If compounds of formula I are ingested by adult insect stages with the feed, then a diminished oviposition and/or reduced hatching rate is observed in many insects, especially in Coleoptera, e.g. *Anthonomus grandis.*

The compounds of formula I can also be used for controlling ectoparasites such as *Lucilia sericata,* and ticks, in domestic animals and productive livestock, e.g. by treating animals, cowsheds, barns, stables etc., and pastures.

The activity of the compounds of formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and *Bacillus thuringiensis* preparations.

The compounds of formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/-polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8-C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyl-trimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ridgewood, N.J., 1979; Dr. Helmut Stache, "Tensid Taschenbuch" (Handbook of Surfactants), Carl Hanser Verlag, Munich/Vienna, 1981.

The pesticidal compositions usually contain 0.1 to 99 %, preferably 0.1 to 95 %, of a compound of formula I or combination thereof with other insecticides or acaricides, 1 to 99.9 % of a solid or liquid adjuvant, and 0 to 25 %, preferably 0.1 to 20 %, of a surfactant.

Whereas commercial products are preferably formulated as concentrates, the end user will normally employ dilute formulations of substantially lower concentration.

The compositions may also contain further ingredients, such as stabilisers, antifoams, viscosity regulators, binders, tackifiers as well as fertilisers or other active ingredients in order to obtain special effects.

Example 1:

(a) Preparation of 2,6-diethyl-4-(6'-chloropyridazin-3'-yloxy)-aniline 17.3 g of 2,6-diethyl-4-hydroxyaniline and 23.2 g of pulverised potassium carbonate are stirred in 80 ml of dimethylsulfoxide for 30 minutes at room temperature. The mixture is then heated to 80°–90° C. and a solution of 14.9 g of 3,6-dichloropyridazine in 20 ml of dimethylsulfoxide is added dropwise. The reaction mixture is subsequently stirred for 12 hours at 80°–90° C. For working up, the bulk of the solvent is removed under a high vacuum and the residue is taken up in 200 ml of dichloromethane and 100 ml of water. The organic phase is washed with 100 ml of water, dried over sodium sulfate and the solvent is removed, affording a brown oil. For purification, this crude product is taken up in c. 500 ml of a mixture of dichloromethane and ethyl acetate (volume ratio 9:1) and filtered through a column of silica gel.

The pure fractions are concentrated by evaporation, to give the title compound of formula

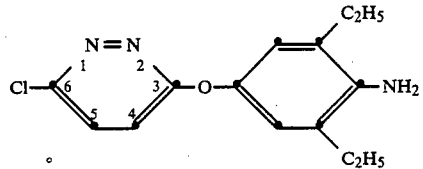

in the form of a yellowish oil (compound 1.1).

The following anilines of formula V are prepared in analogous manner:

| Compound | Formula | m.p. |
|---|---|---|
| 1.2 | ![structure] | 199–201° C. |
| 1.3 | ![structure] | 161–163° C. |

-continued

| Compound | Formula | m.p. |
|---|---|---|
| 1.4 | (pyrimidine with Cl, -O- linked to 2,6-dimethyl-4-aminophenyl) | 155–157° C. |
| 1.5 | (6-chloroquinazoline, -O- linked to 2,6-dimethyl-4-aminophenyl) | 153–165.5° C. (contains c. 10% of 7-Cl isomer) |
| 1.6 | (6-fluoroquinazoline, -O- linked to 2,6-dimethyl-4-aminophenyl) | 166–170° C. |
| 1.7 | (6-trifluoromethylquinazoline, -O- linked to 2,6-dimethyl-4-aminophenyl) | 140–142° C. |
| 1.8 | (pyrimidine with CF$_3$, -O- linked to 2,6-dimethyl-4-aminophenyl) | 142–144° C. |
| 1.9 | (quinoline, -O- linked to 2,6-dimethyl-4-aminophenyl) | 182–184° C. |
| 1.10 | (6-chloroquinoline, -O- linked to 2,6-dimethyl-4-aminophenyl) | 159–161° C. |

| Compound | Formula | m.p. |
|---|---|---|
| 1.11 | | 198–200° C. (dec.) |
| 1.12 | | 110–111° C. |
The following anilines of formula V can also be obtained as indicated above:
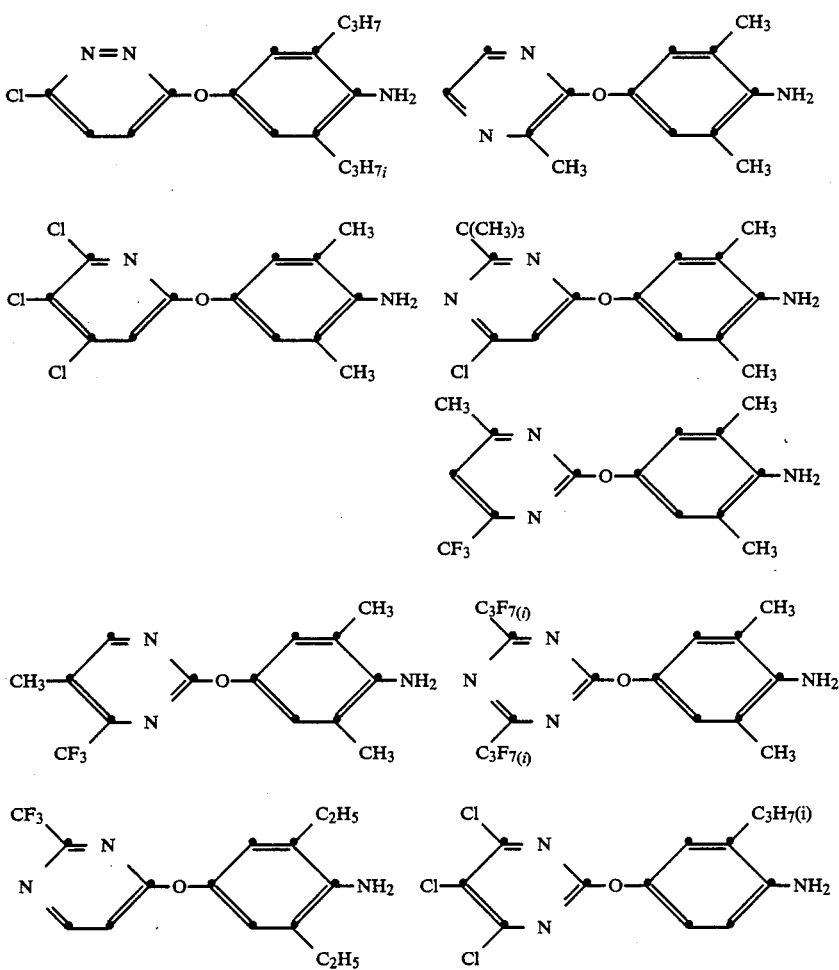

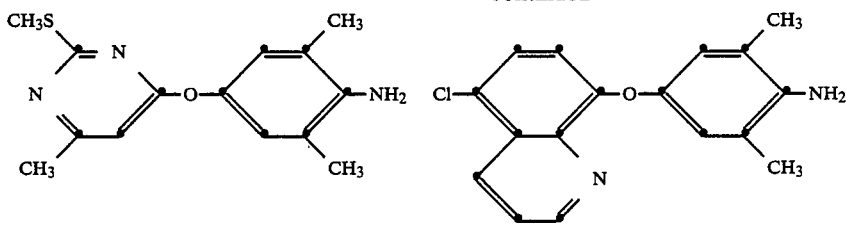

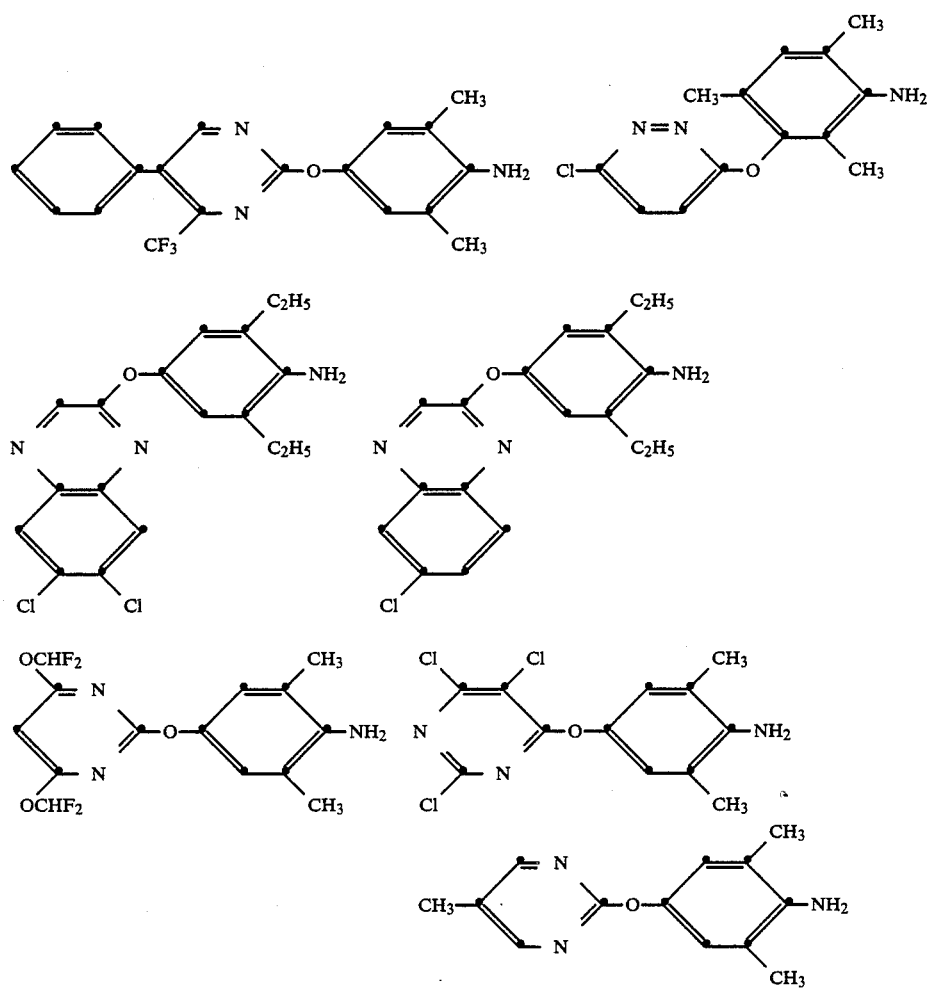

(b) Preparation of 2,6-diethyl-4-(6'chloropyridazin-3'-yloxy)phenylisothiocyanate 25.8 g of thiophosgene and 37.5 g of calcium carbonate are stirred in 300 ml of dichloromethane and 190 ml of water, a solution of 52.0 g of 2,6-diethyl-4-(6'-chloropyridazin-3'-yloxy)aniline in 200 ml of dichloromethane is added dropwise at 0°-5° C. to this mixture.

The reaction mixture is stirred for 5 hours at room temperature and then filtered. The organic phase is separated from the filtrate, washed with 2×100 ml of water, dried over sodium sulfate and concentrated by evaporation. The solid residue is recrystallized from c. 100 ml of hot hexane, affording the title compound of formula

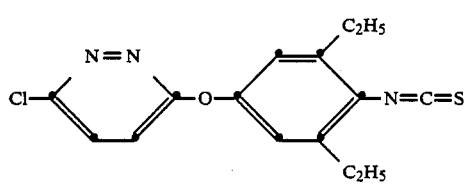

as a pale brown cryatalline product with a melting point of 102°-104° C. (compound 2.1).

The following isothiocyanates of formula II are prepared in analogous manner:

| Compound | Formula | m.p. |
|---|---|---|
| 2.2 | (pyrimidin-2-yl)-O-(2,6-dimethyl-4-isothiocyanatophenyl) | 102–104° C. |
| 2.3 | (6-chloropyridazin-3-yl)-O-(2,6-dimethyl-4-isothiocyanatophenyl) | 129–131° C. |
| 2.4 | (6-trifluoromethylquinoxalin-2-yl)-O-(2,6-dimethyl-4-isothiocyanatophenyl) | 118–120° C. |
| 2.5 | (7-chloroquinoxalin-2-yl)-O-(2,6-dimethyl-4-isothiocyanatophenyl) | 126–127° C. |
| 2.6 | (6-fluoroquinolin-2-yl)-O-(2,6-dimethyl-4-isothiocyanatophenyl) | 128–133° C. |
| 2.7 | (6-trifluoromethylpyrazin-2-yl)-O-(2,6-dimethyl-4-isothiocyanatophenyl) | 158–161° C. |
| 2.8 | (quinolin-2-yl)-O-(2,6-dimethyl-4-isothiocyanatophenyl) | 145–146° C. |

| Compound | Formula | m.p. |
|---|---|---|
| 2.9 | | 110–111° C. |
| 2.10 | | 135–136° C. |
| 2.11 | | 105–107° C. |

(c) preparation of
N-2,6-diethyl-4-(6'-chloropyridazin-3'-yloxy)-phenyl-N-'-isopropylthiourea A mixture of 23.0 g of 2,6-diethyl-4-(6'-chloropyridazin-3'-yloxy)-phenylisothiocyanate and 12.8 g of isopropylamine is stirred in 100 ml of toluene for 12 hours at room temperature. The reaction mixture is then concentrated to a small volume and left to crystallize after addition of hexane. The crystals are filtered with suction and dried, affording the title compound of formula

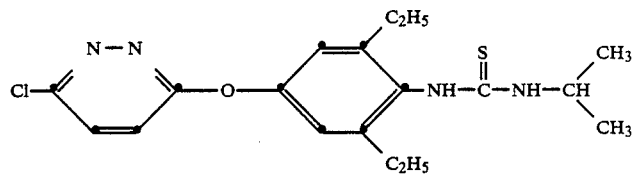

as a pale brown crystalline product with a melting point of 174°–176° C. (compound 3.1).

The following thioureas of formula I are obtained in analogous manner:

| Compound | Formula | m.p. |
|---|---|---|
| 3.2 | | 142–144° C. |
| 3.3 | | 188° C. |

| Compound | Formula | m.p. |
|---|---|---|
| 3.4 | (4-Cl-2,6-disubstituted pyrimidin-2-yl)-O-(2,6-dimethylphenyl)-NH-C(=S)-NH-C(CH₃)₃ | 140–141,5° C. |
| 3.5 | (4-F-2,6-disubstituted pyrimidin-2-yl)-O-(2,6-dimethylphenyl)-NH-C(=S)-NH-C(CH₃)₃ | 148–150° C. |
| 3.6 | (4-CF₃-2,6-disubstituted pyrimidin-2-yl)-O-(2,6-dimethylphenyl)-NH-C(=S)-NH-C(CH₃)₃ | 148–150° C. |
| 3.7 | (6-Cl-pyridazin-3-yl)-O-(2,6-dimethylphenyl)-NH-C(=S)-NH-CH(CH₃)₂ | 184–185° C. |
| 3.8 | (quinolin-2-yl)-O-(2,6-dimethylphenyl)-NH-C(=S)-NH-C(CH₃)₃ | 143–144° C. |
| 3.9 | (pyrimidin-2-yl)-O-(2,6-diethylphenyl)-NH-C(=S)-NH-C(CH₃)₃ | 153° C. (dec.) |
| 3.10 | (pyrimidin-2-yl)-O-(2,6-diethylphenyl)-NH-C(=S)-NH-CH(CH₃)₂ | 120–125° C. (dec.) |
| 3.11 | (5-Cl-pyrimidin-2-yl)-O-(2,6-diethylphenyl)-NH-C(=S)-NH-C(CH₃)₃ | 139–140° C. (dec.) |

-continued
| Compound | Formula | m.p. |
|---|---|---|
| 3.12 | 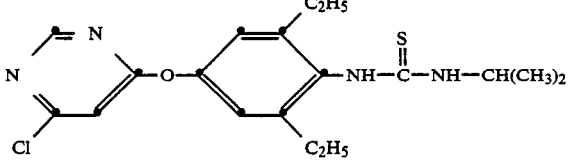 | 165–167° C. |
| 3.13 | 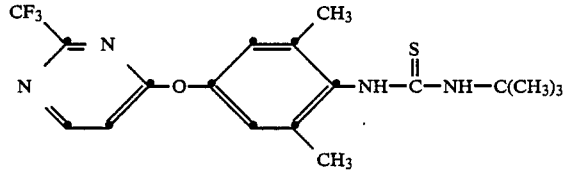 | 142–144° C. |
| 3.14 | 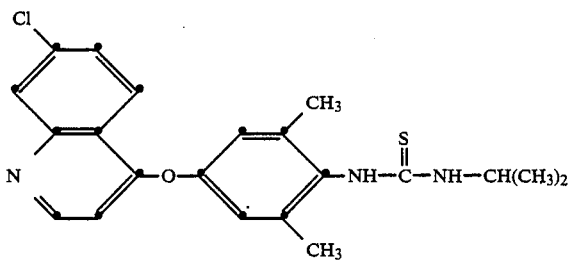 | 170–175,5° C. (dec.) |
| 3.15 | 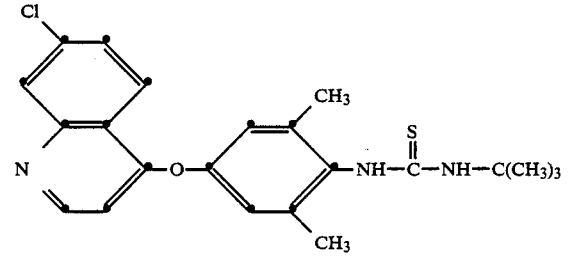 | 158–162° C. (dec.) |
| 3.16 | 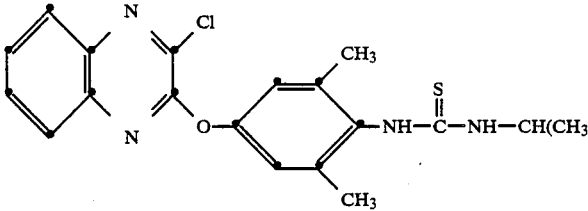 | 200–203° C. (dec.) |
| 3.17 | 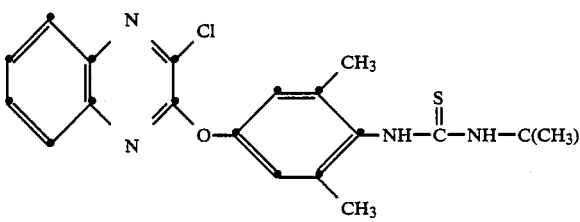 | 175–180° C. (dec.) |
| 3.18 | 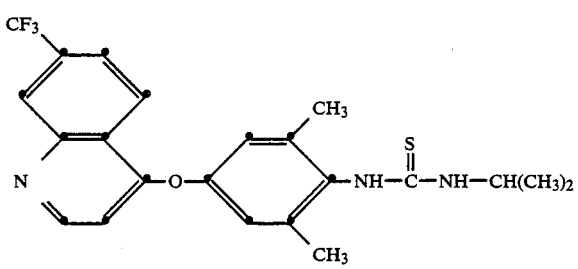 | 181–185° C. (dec.) |

-continued
| Compound | Formula | m.p. |
|---|---|---|
| 3.19 | 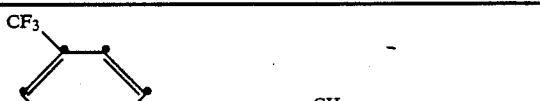 | 168-173° C. (dec.) |
The following thioureas of formula I can also be obtained as indicated above:
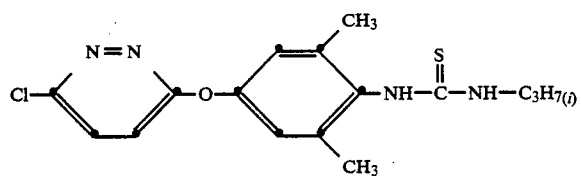
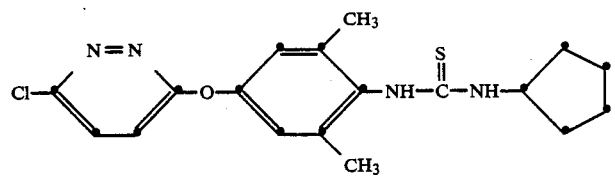
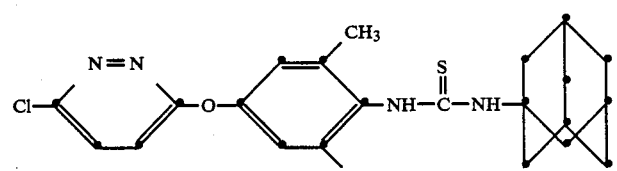
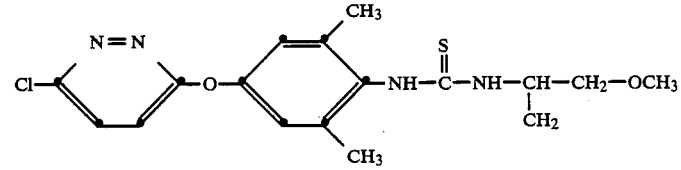
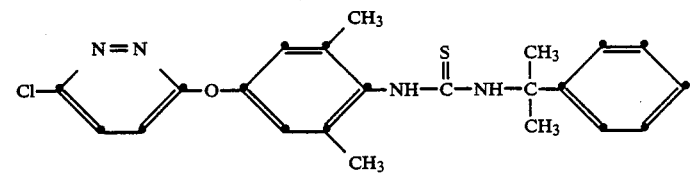
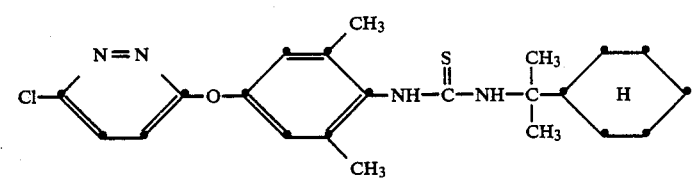
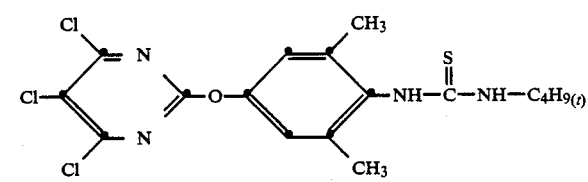

-continued
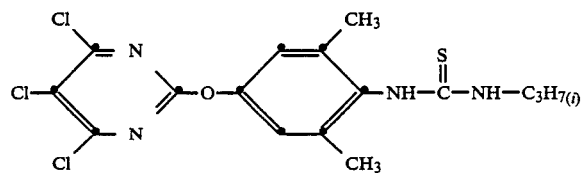
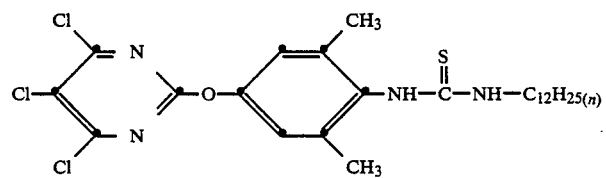
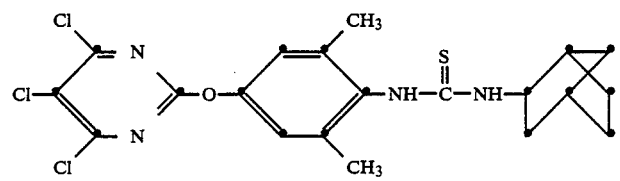
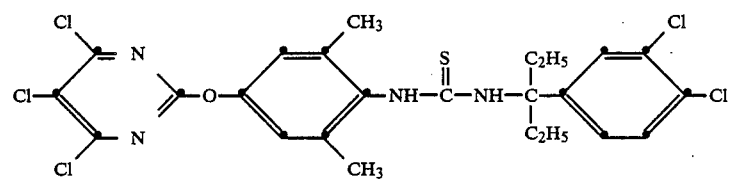
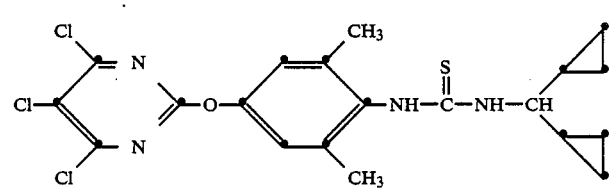
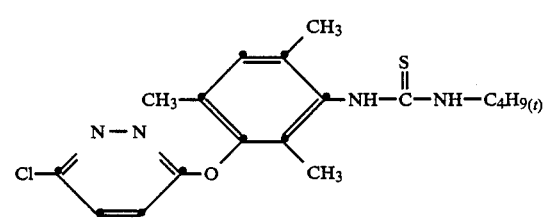
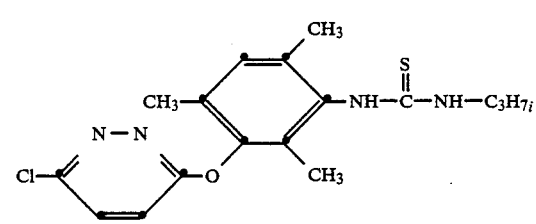
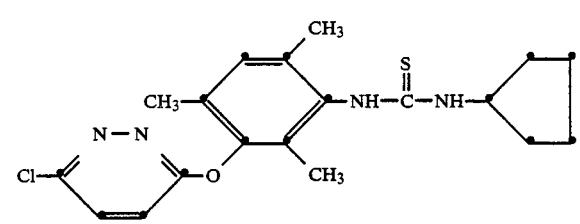

-continued
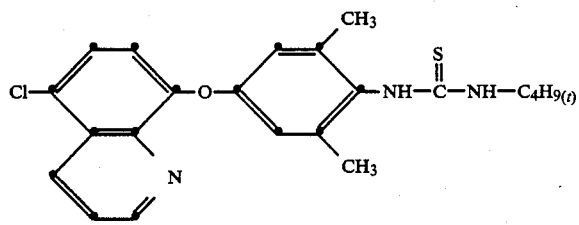
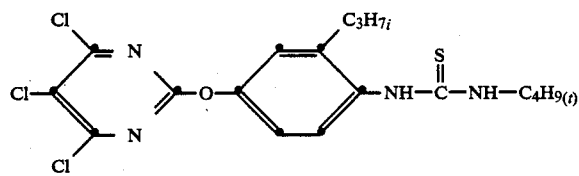
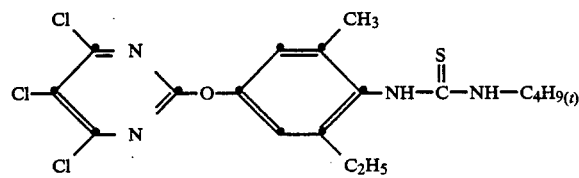
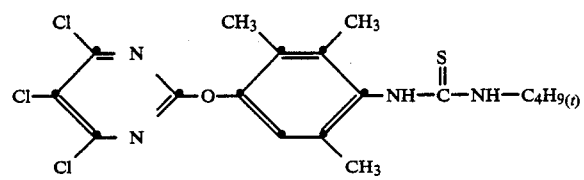
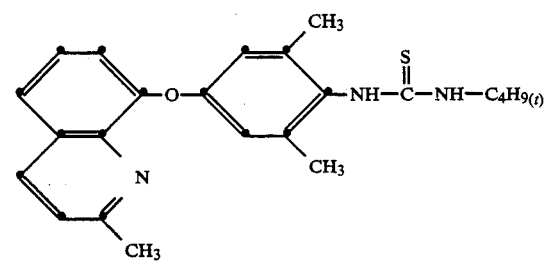
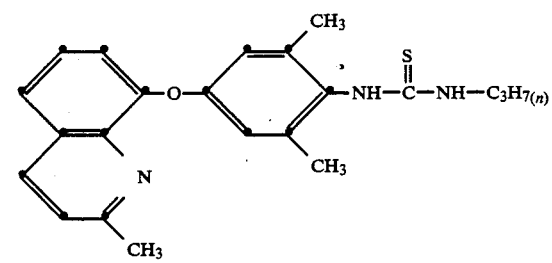
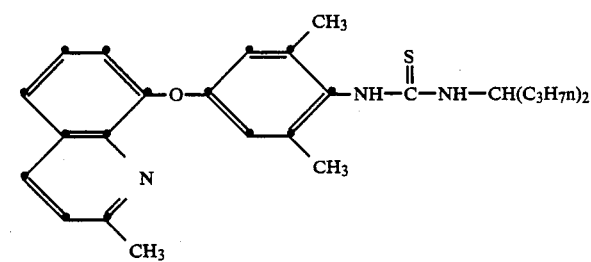

-continued
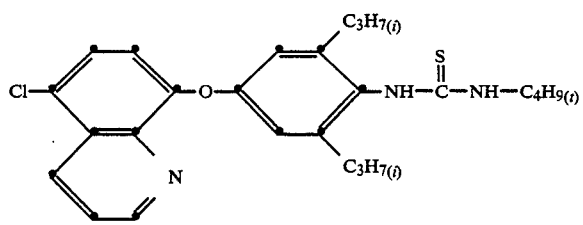
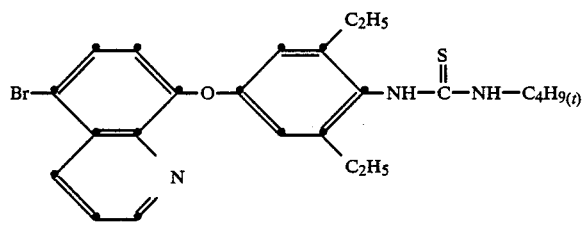
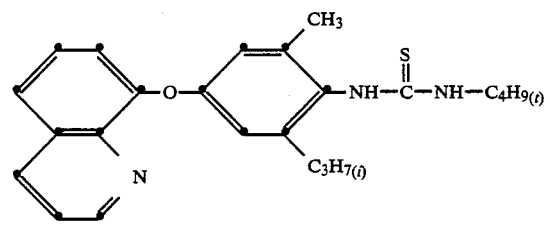
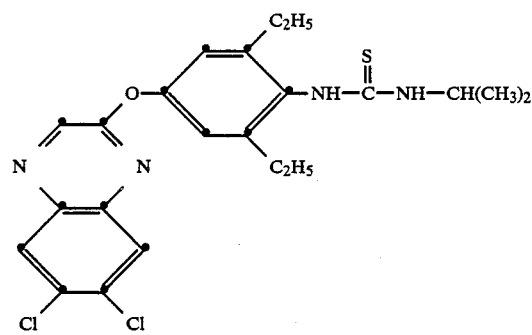
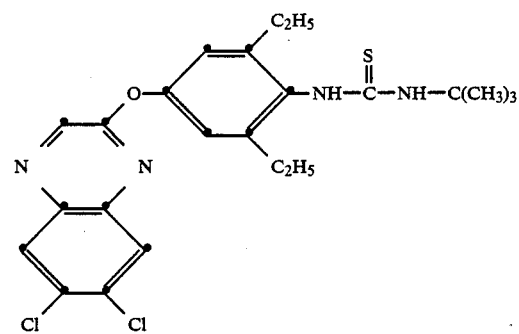

-continued

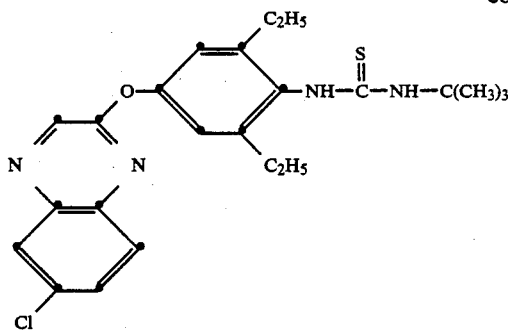

Example 2: Preparation of N-2,6-dimethyl-4-(pyrimidin-2'-yloxy)-phenyl-N'-tert-butyl-S-methylisothiourea 2.8 of methyl iodide are added to 5.0 g on N-2,6-dimethyl-4-(pyrimidinin-2'-yloxy)phenyl-N'-tert-butyl-thiourea in 40 ml of absolute ethanol and the reaction mixture is stirred for 40 hours under gentle reflux. The resultant reaction solution is concentrated by evaporation and the residue is taken up in dichloromethane and 10% aqueous sodium carbonate solution. The organic phase is washed with water, dried over sodium sulfate and concentrated to a small volume. This concentrated solution is filtered through a column of silica gel and washed with dichloromethane. The filtrate is then concentrated by evaporation, affording the title compound of formula

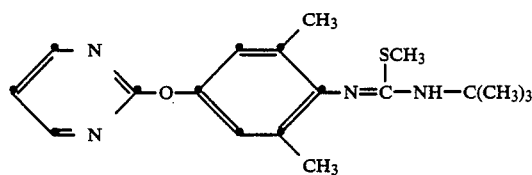

as a solid with a melting point of 174°–176° C. (compound 4.1).

The following isothioureas of formula I are prepared in analogous manner:

| Compound | Formula | physical data |
|---|---|---|
| 4.2 | ![structure] | yellowish oil |
| 4.3 | ![structure] | m.p. = 105–107° C. |
| 4.4 | ![structure] | m.p. = 114–116° C. |
| 4.5 | ![structure] | m.p. = 126–128° C. |

-continued

| Compound | Formula | |
|---|---|---|
| 4.6 | [structure: 5-CF₃-2,3-diaza... pyrazine-O-phenyl(2,6-diCH₃)-N=C(SCH₃)-NH-C(CH₃)₃] | m.p. = 121–123° C. |
| 4.7 | [structure: Cl-pyridazine(N=N)-O-phenyl(2,6-diCH₃)-N=C(SCH₃)-NH-CH(CH₃)₂] | m.p. = 111–113° C. |
| 4.8 | [structure: quinoline-O-phenyl(2,6-diCH₃)-N=C(SCH₃)-NH-C(CH₃)₃] | m.p. = 113–115°30 C. |
| 4.9 | [structure: pyrimidine-O-phenyl(2,6-diC₂H₅)-N=C(SCH₃)-NH-C(CH₃)₃] | m.p. = 135–136° C. |
| 4.10 | [structure: pyrimidine-O-phenyl(2,6-diC₂H₅)-N=C(SCH₃)-NH-CH(CH₃)₂] | m.p. = 99–101° C. |
| 4.11 | [structure: 5-Cl-pyrimidine-O-phenyl(2,6-diC₂H₅)-N=C(SCH₃)-NH-C(CH₃)₃] | resinous substance |
| 4.12 | [structure: 5-Cl-pyrimidine-O-phenyl(2,6-diC₂H₅)-N=C(SCH₃)-NH-CH(CH₃)₂] | $n_D^{38}$ = 1.5774 |
| 4.13 | [structure: 4-CF₃-pyrimidine-O-phenyl(2,6-diCH₃)-N=C(SCH₃)-NH-C(CH₃)₃] | m.p. = 87–89° C. |

| Compound | Formula | |
|---|---|---|
| 4.14 | (4-chloro-pyridin-2-yl)-O-(2,6-dimethylphenyl)-N=C(SCH₃)-NH-CH(CH₃)₂ | 46,5–53,5° C. |
| 4.15 | (4-chloro-pyridin-2-yl)-O-(2,6-dimethylphenyl)-N=C(SCH₃)-NH-C(CH₃)₃ | 117–120° C. |
| 4.16 | (3-chloro-quinoxalin-2-yl)-O-(2,6-dimethylphenyl)-N=C(SCH₃)-NH-CH(CH₃)₂ | 120–121,5° C. (HI-salt: m.p. = 171–176° C. dec.) |
| 4.17 | (3-chloro-quinoxalin-2-yl)-O-(2,6-dimethylphenyl)-N=C(SCH₃)-NH-C(CH₃)₃ | 136–141.5° C. |
| 4.18 | (4-trifluoromethyl-pyridin-2-yl)-O-(2,6-dimethylphenyl)-N=C(SCH₃)-NH-CH(CH₃)₂ | 45–50° C. |
| 4.19 | (4-trifluoromethyl-pyridin-2-yl)-O-(2,6-dimethylphenyl)-N=C(SCH₃)-NH-C(CH₃)₃ | |

The following isothioureas of formula I as well as the hydrogen iodide, oxalic acid and phenylsulfonic acid salts thereof can also be prepared as indicated above:

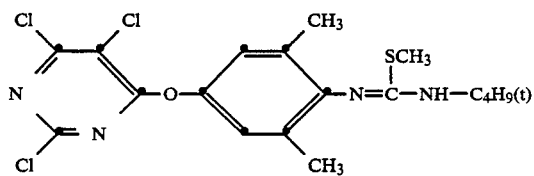
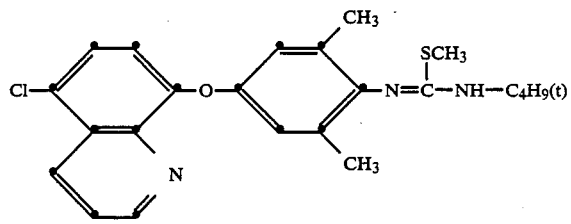
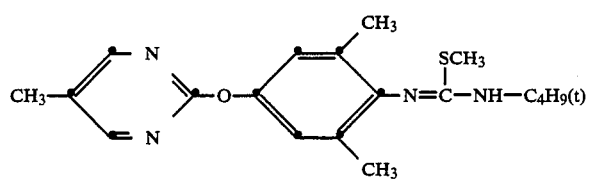
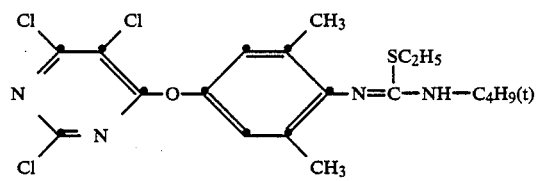
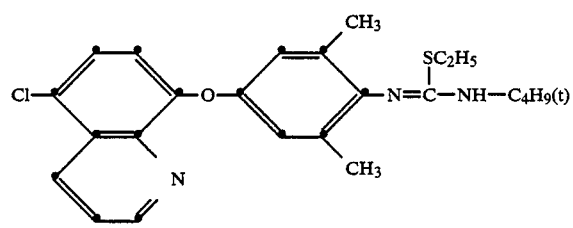
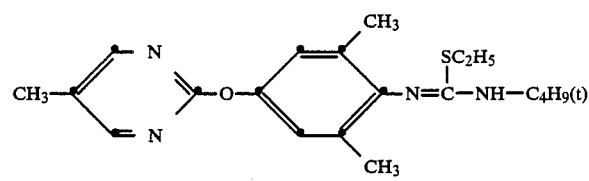
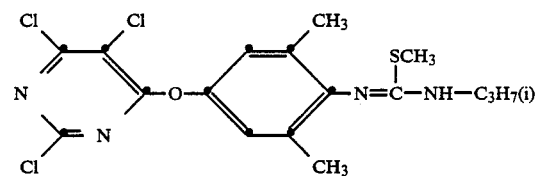
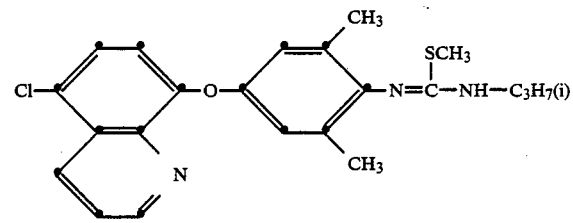

-continued
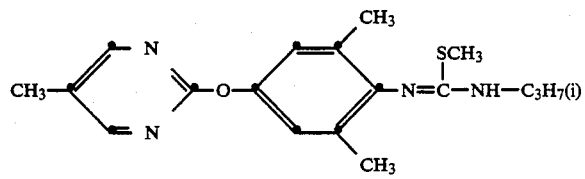
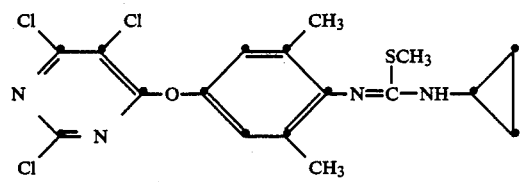
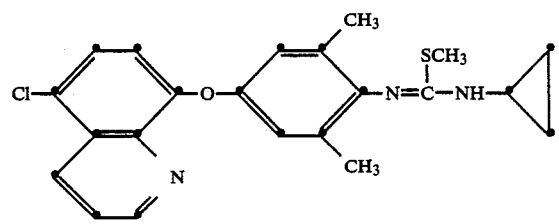
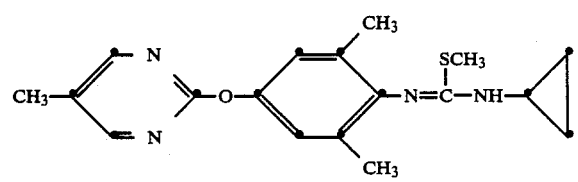
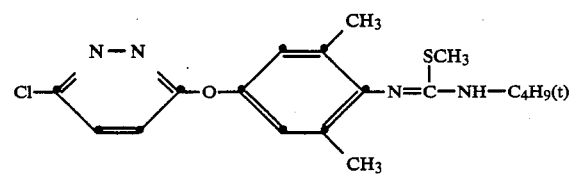
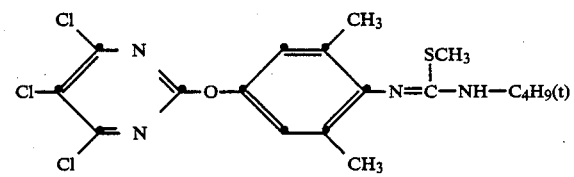
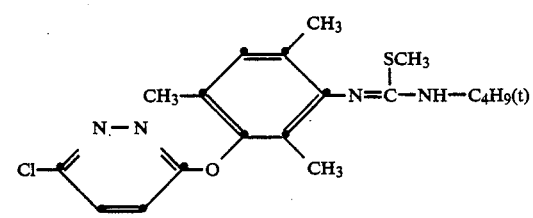
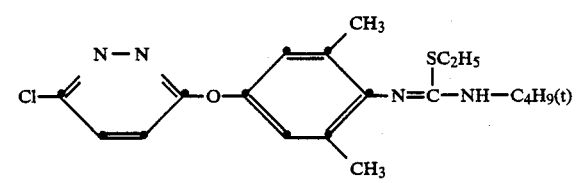

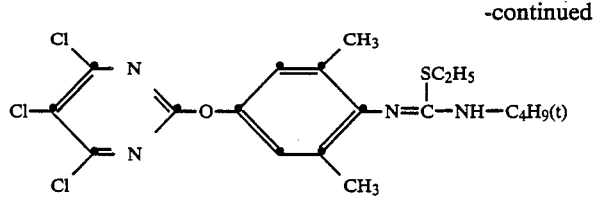
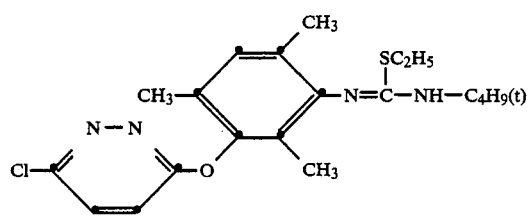
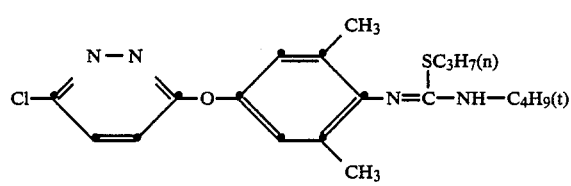
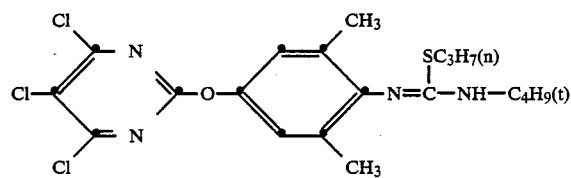
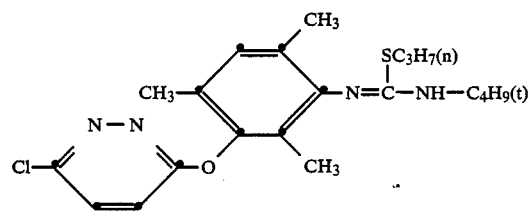
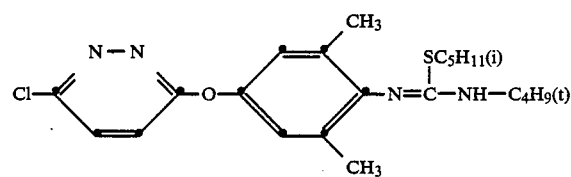
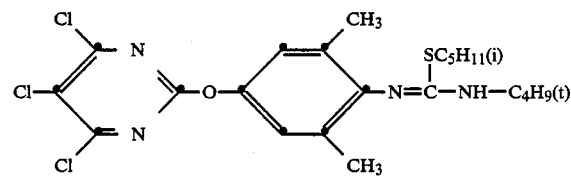
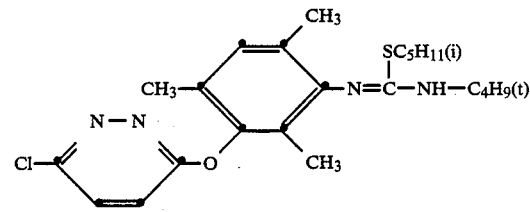

-continued
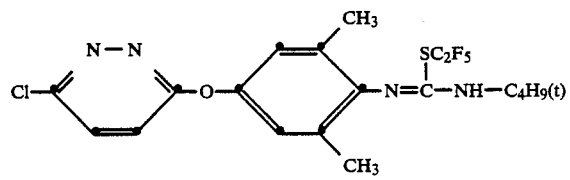
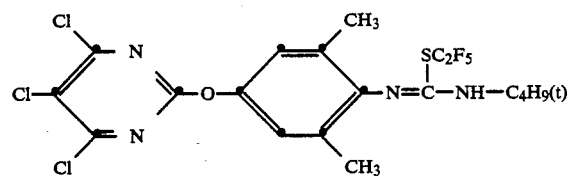
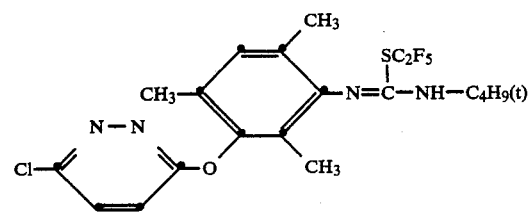
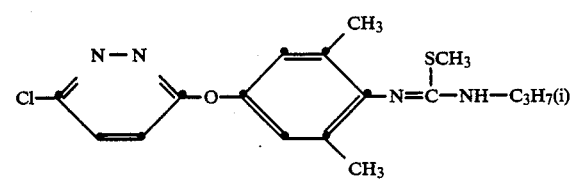
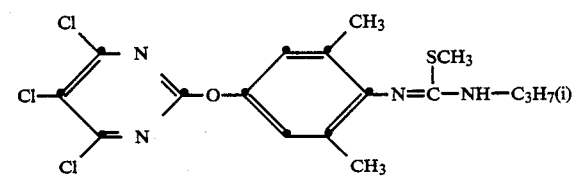
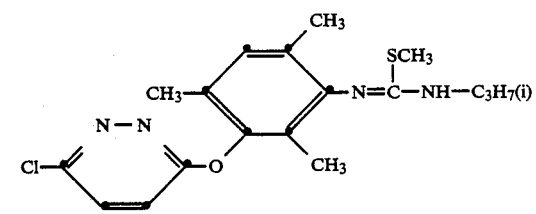
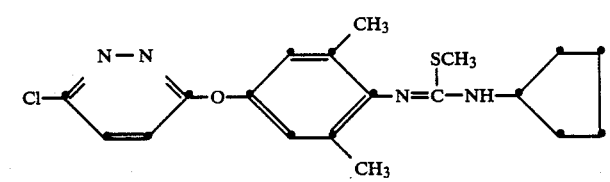
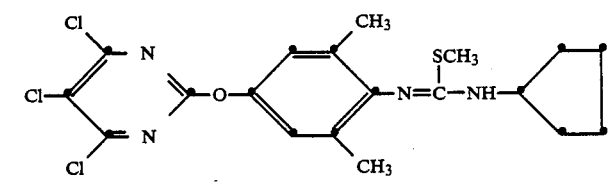

-continued
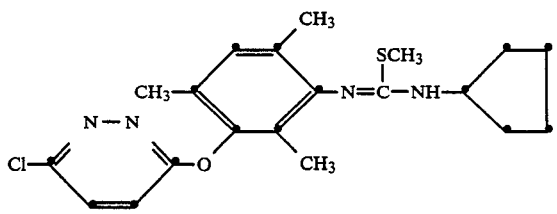
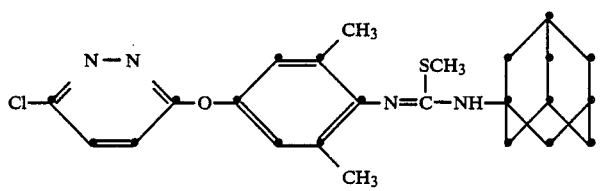
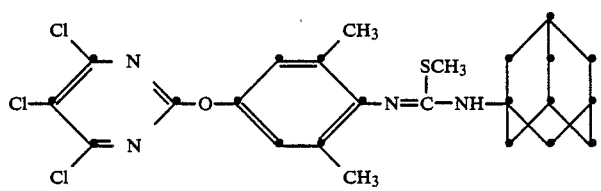
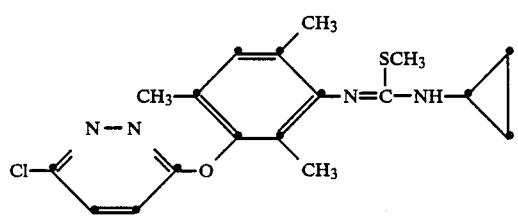
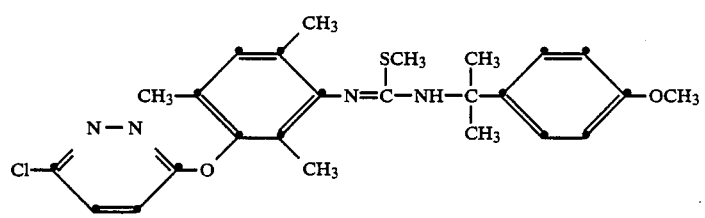
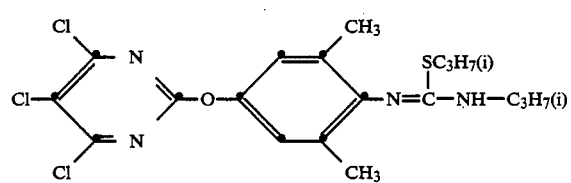
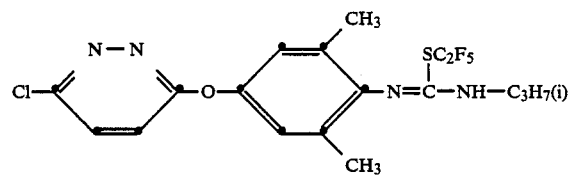

-continued

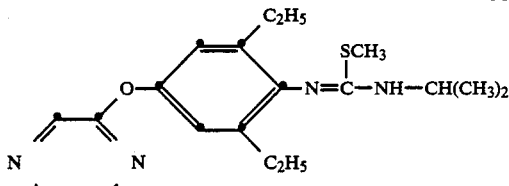
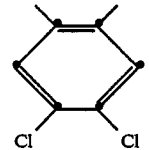

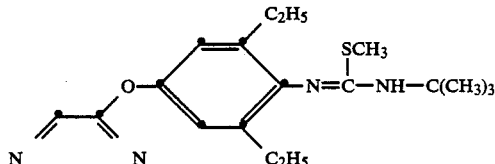
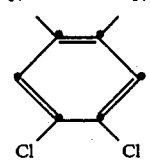

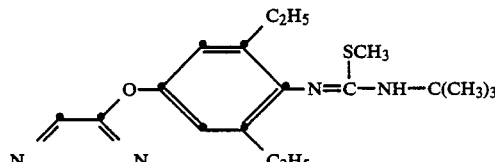
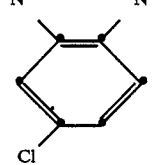

Example 3: Preparation of N-2,6-diethyl-4-(6'-chloropyridazin-3'-yloxy)phenyl--N'-isopropylcarbodiimide 9.85 g of N-2,6-diethyl-4-(6'-chloropyridazin-3'-yloxy)phenyl-N'-isopropylthiourea and 6.65 g of 2-chloro-1-methylpyridinium iodide are added to 50 ml of acetonitrile. With stirring, a solution of 6.6 g of triethylamine in 70 ml of acetonitrile is added dropwise at room temperature and the reaction mixture is stirred for 12 hours under gentle reflux. The reaction mixture is then concentrated at 50° C. by rotary evaporation. The residue is taken up in 1000 ml of hexane, the solution is washed twice with water, dried over sodium sulfte, filtered and concentrated by evaporation, affording the title compound of formula

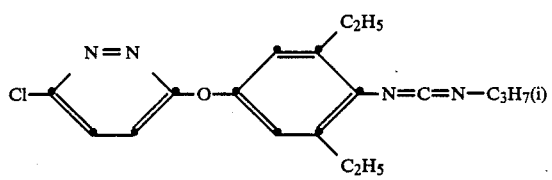

as a pale yellowish product with a melting point of 87°–89° C. (compound 5.1).

The following carbodiimides of formula I are prepared in analogous manner:

| Compound | Formula | physical data |
|---|---|---|
| 5.2 | ![structure] | 110–112° C. |

-continued

| Compound | Formula | |
|---|---|---|
| 5.3 | [structure: 3-chloro-pyridazinyl-O-(2,6-dimethyl-4-(N=C=N-C(CH₃)₃)phenyl)] | 100–101.5° C. |
| 5.4 | [structure: 3-trifluoromethyl-pyridazinyl-O-(2,6-dimethyl-4-(N=C=N-C(CH₃)₃)phenyl)] | 107–109° C. |
| 5.5 | [structure: Cl-C=C-N=N-C=... -O-(2,6-dimethyl-4-(N=C=N-C(CH₃)₃)phenyl)] | 84–86° C. |
| 5.6 | [structure: pyridazinyl-O-(2,6-dimethyl-4-(N=C=N-CH(CH₃)₂)phenyl)] | 76–79° C. |
| 5.7 | [structure: pyrimidinyl-O-(2,6-diethyl-4-(N=C=N-C(CH₃)₃)phenyl)] | 106–107° C. |
| 5.8 | [structure: pyrimidinyl-O-(2,6-diethyl-4-(N=C=N-CH(CH₃)₂)phenyl)] | 78–80° C. |
| 5.9 | [structure: 5-chloro-pyrimidinyl-O-(2,6-diethyl-4-(N=C=N-C(CH₃)₃)phenyl)] | $n_D^{23} = 1.5688$ |
| 5.10 | [structure: 5-chloro-pyrimidinyl-O-(2,6-diethyl-4-(N=C=N-CH(CH₃)₂)phenyl)] | $n_D^{23} = 1.5775$ |

-continued

| Compound | Formula | |
|---|---|---|
| 5.11 | [structure: CF3-pyrimidine-O-(2,6-dimethylphenyl)-N=C=N-C(CH3)3] | m.p. = 67–69° C. |
| 5.12 | [structure: 4-chloroquinoline-O-(2,6-dimethylphenyl)-N=C=N-CH(CH3)2] | m.p. = 67–69,5° C. |
| 5.13 | [structure: 4-chloroquinoline-O-(2,6-dimethylphenyl)-N=C=N-C(CH3)3] | m.p. = 103–107° C. |
| 5.14 | [structure: chloroquinoxaline-O-(2,6-dimethylphenyl)-N=C=N-CH(CH3)2] | m.p. = 64–67,5° C. |
| 5.15 | [structure: chloroquinoxaline-O-(2,6-dimethylphenyl)-N=C=N-C(CH3)3] | m.p. = 64,5–68° C. |
| 5.16 | [structure: CF3-quinoline-O-(2,6-dimethylphenyl)-N=C=N-CH(CH3)2] | m.p. 68–70° C. |

| Compound | Formula | |
|---|---|---|
| 5.17 | | 69–71° C. |
The following carbodiimides of formula I can also be prepared as indicated above:
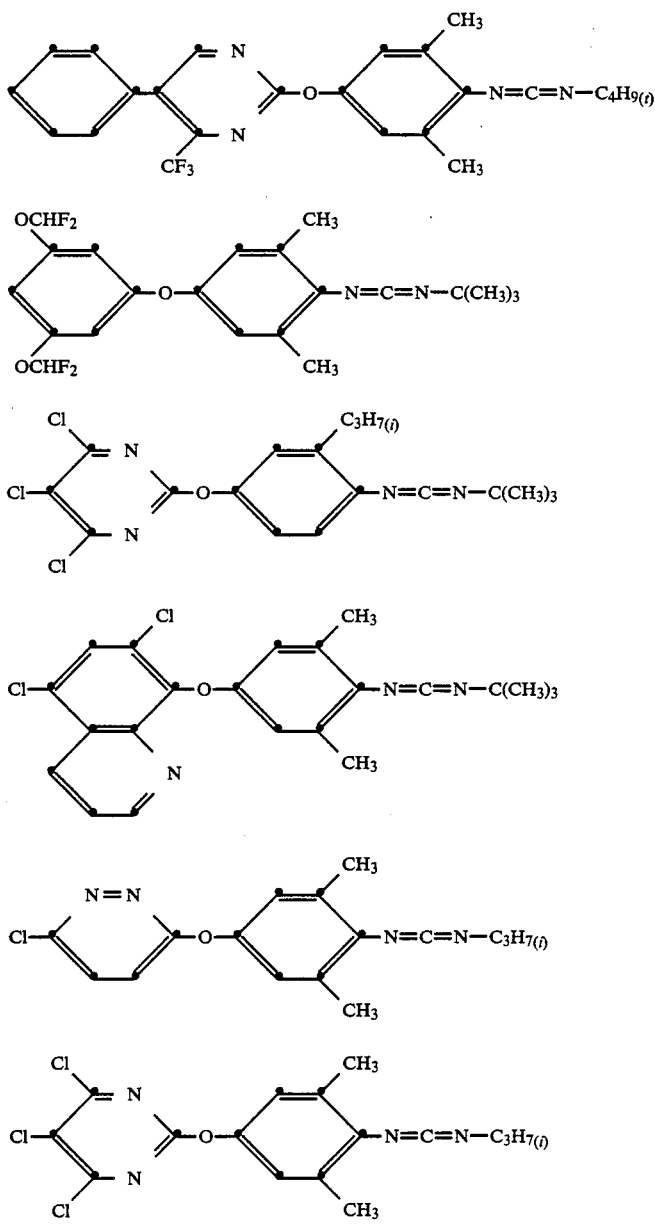

-continued
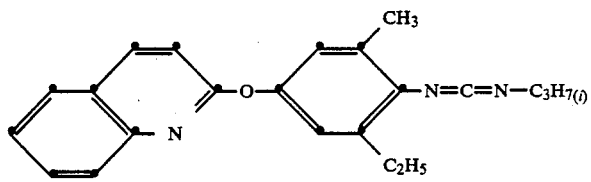
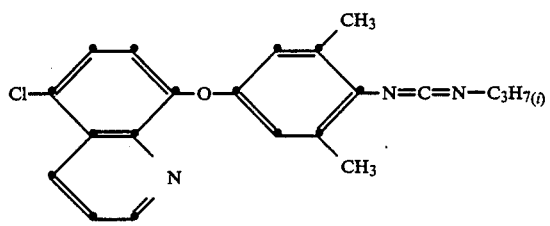
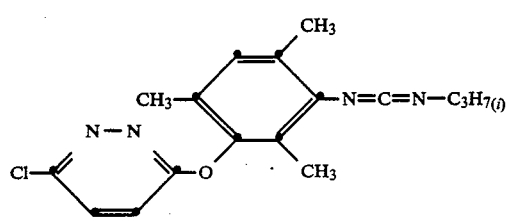
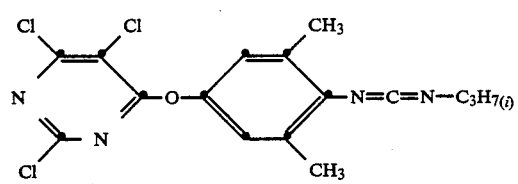
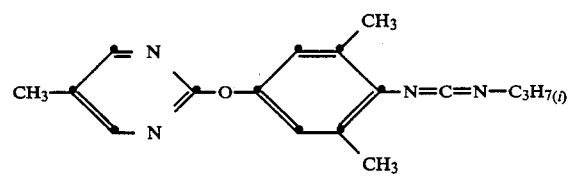
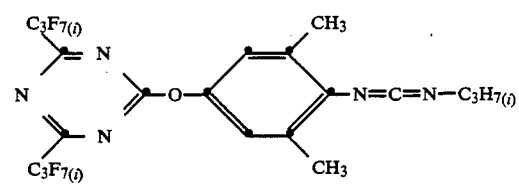
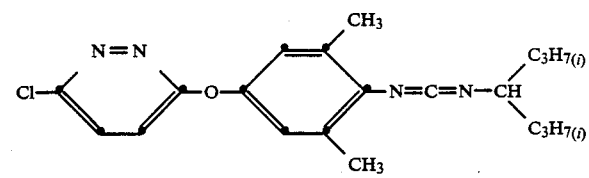
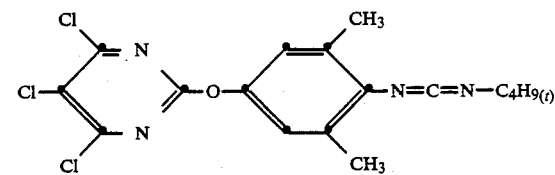

-continued
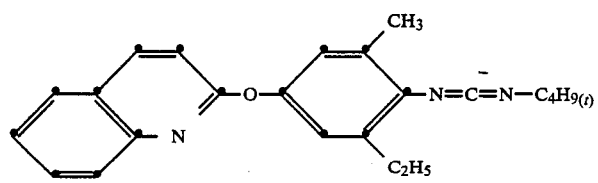
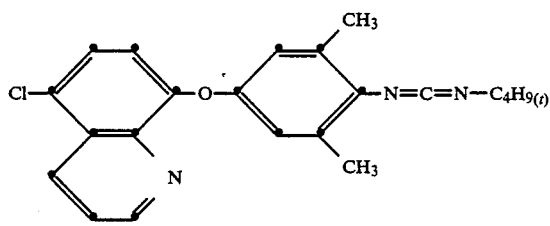
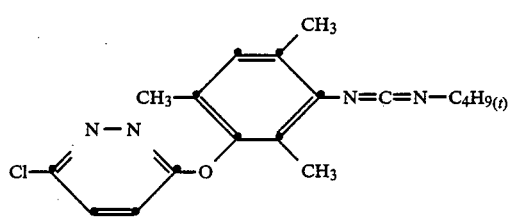
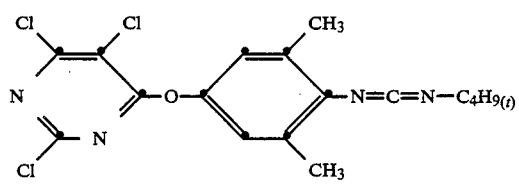
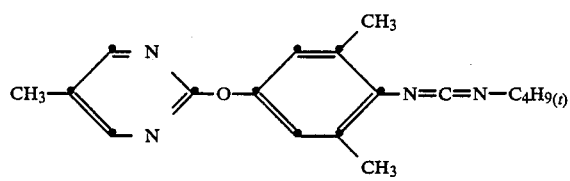
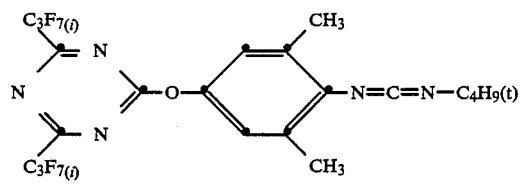
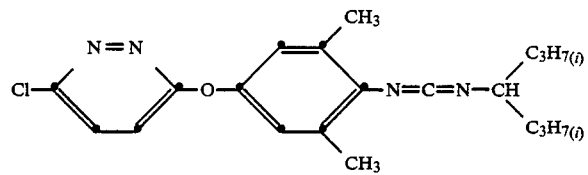
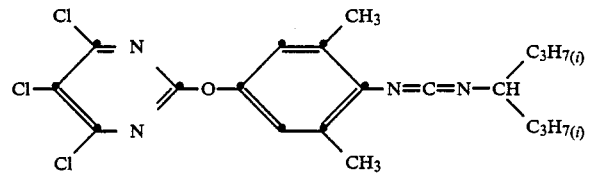

-continued
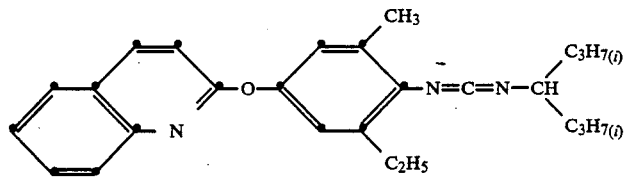
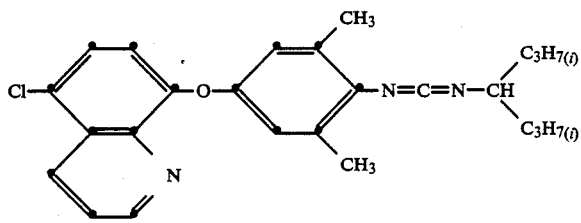
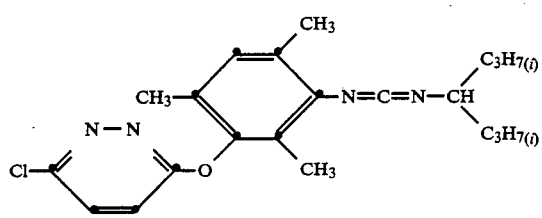
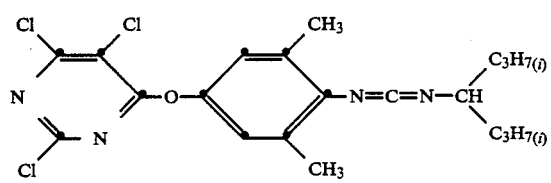
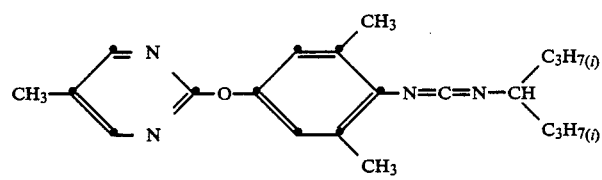
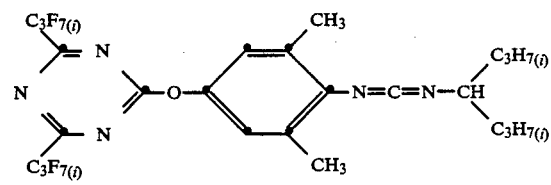
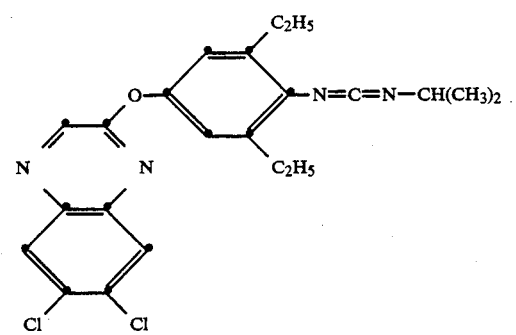

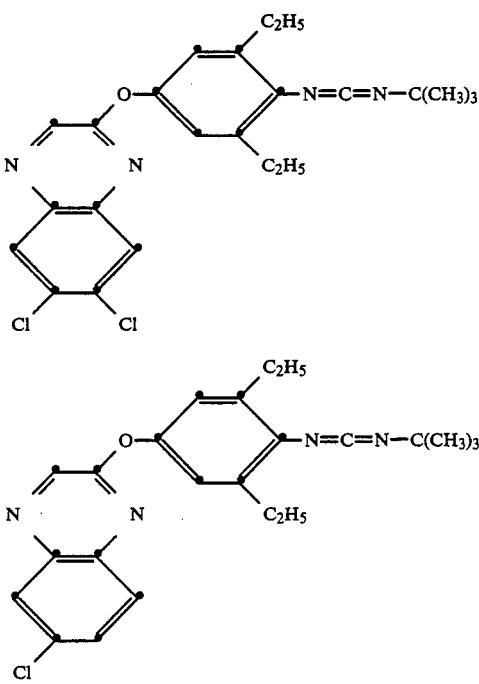

Example 4:

Formulations for liquid active ingredients of formula I according to Examples 1 to 3 or combinations thereof with other insecticides or acaricides (throughout, percentages are by weight)

| 4.1 Emulsifiable concentrates | (a) | (b) | (c) |
|---|---|---|---|
| active ingredient or active ingredient combination | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexane | — | 15% | 20% |
| xylene mixture | 65% | 25% | 20% |

Emulsions of any required concentration can be produced from such concentrates by dilution with water.

| 4.2 Solutions | (a) | (b) | (c) | (d) |
|---|---|---|---|---|
| active ingredient or active ingredient combination | 80% | 10% | 5% | 95% |
| ethylene glycol monomethyl ether | 20% | — | — | — |
| polyethylene glycol 400 | — | 70% | — | — |
| N-methyl-2-pyrrolidone | — | 20% | — | — |
| expoxidised coconut oil | — | — | 1% | 5% |
| ligroin (boiling range 160–190°) | — | — | 94% | — |

These solutions are suitable for application in the form of microdrops.

| 4.3 Granulates | (a) | (b) |
|---|---|---|
| active ingredient or active ingredient combination | 5% | 10% |
| kaolin | 94% | — |
| highly dispersed silicic acid | 1% | — |
| attapulgite | — | 90% |

The active ingredient or active ingredient combination is dissolved in methylene chloride, the solution is sprayed onto the carrier, and the solvent is subsequently removed by evaporation under vacuum.

| 4.4 Dusts | (a) | (b) |
|---|---|---|
| active ingredient or active ingredient combination | 2% | 5% |
| highly dispersed silicic acid | 1% | 5% |
| talcum | 97% | — |
| kaolin | — | 90% |

Ready for use dusts are obtained by intimately mixing the carriers the active ingredient or active ingredient combination.

Formulations for solid active ingredients of formula I according to Examples 1 to 3 or combinations thereof with other insecticides or acaricides (throughout, percentages are by weight)

| 4.5 Wettable powders | (a) | (b) | (c) |
|---|---|---|---|
| active ingredient or active ingredient combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient or active ingredient combination is thoroughly mixed with the adjuvants and the mixture is thoroughly ground in a suitable mill, affording wettable powders which can be diluted with water to give suspensions of any desired concentration.

| 4.6 Emulsifiable concentrate | |
|---|---|
| active ingredient or active ingredient combination | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 4.7 Dusts | (a) | (b) |
|---|---|---|
| active ingredient or active ingredient combination | 5% | 8% |
| talcum | 95% | — |
| kaolin | — | 92% |

Ready for use dusts are obtained by mixing the active ingredient or active ingredient combination with the carrier, and grinding the mixture in a suitable mill.

| 4.8 Extruder granulate | |
|---|---|
| active ingredient or active ingredient combination | 10% |
| sodium lignosulfonate | 2% |
| carboxymethylcellulose | 1% |
| kaolin | 87% |

The active ingredient or active ingredient combination is mixed and ground with the adjuvants, and the mixture is subsequently moistened with water. The mixture is extruded, granulated and then dried in a stream of air.

| 4.9 Coated granulate | |
|---|---|
| active ingredient or active ingredient combination | 3% |
| polyethylene glycol 200 | 3% |
| kaolin | 94% |

The finely ground active ingredient or active ingredient combination is uniformly applied, in a mixer, to the kaolin moistened with polyethylene glycol. Non-dusty coated granulates are obtained in this manner.

| 4.10 Suspension concentrate | |
|---|---|
| active ingredient or active ingredient combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or active ingredient combination is intimately mixed with the adjuvants, giving a suspension concentrate from which suspensions of any desired concentration can be obtained by dilution with water.

Example 5: Action against *Musca domestica*

50 g of freshly prepared nutrient substrate for maggots are charged into each of a number of beakers. A specific amount of a 1% acetonic solution of the respective test compound is pipetted onto the nutrient substrate present in the beakers to give an active ingredient concentration of 400 ppm. The substrate is then thoroughly mixed and the acetone subsequently allowed to evaporate over a period of at least 20 hours.

Then 25 one-day-old maggots of *Musca domestica* are put into each of the beakers containing the treated nutrient substrate for testing with each test compound at the given concentration. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

The compounds of formula I according to Examples 1 to 3 exhibit good activity in this test.

Example 6: Action against *Lucilia sericata*

1 ml of an aqueous solution containing 0.5% of test compound is added to 9 ml of a culture medium. Then about 30 freshly hatched *Lucilia sericata* larvae are added to the culture medium, and the insecticidal action is determined after 48 and 96 hours by evaluating the mortality rate.

The compounds of formula I according to Examples 1 to 3 exhibit good activity against in this test.

Example 7: Action against *Aëdes aegypti*

A concentration of 400 ppm is obtained by pipetting a specific amount of a 0.1 % solution of the test compound in acetone on to the surface of 150 ml of water in a beaker. After the acetone has evaporated, 30 to 40 two-day-old larvae of *Aëdes aegypti* are put into the beaker containing the test compound. Mortality counts are made after 2 and 7 days.

The compounds of formula I according to Examples 1 to 3 exhibit good activity in this test.

Example 8 Insecticidal action against feeding insects

Cotton plants having a height of about 20 cm are sprayed with aqueous emulsions (obtained from a 10% emulsifiable concentrate) containing the respective test compound in a concentration of 400 ppm. After the spray coating has dried, the cotton plants are populated with *Spodoptera littoralis* and *Heliothis virescens* larvae in the $L_3$-stage. The test is carried out at 24° C. and 60% relative humidity. A mortality count is made at 24 hour intervals and the larvae are also examined for inhibition of development and moulting.

Compounds of formula I according to Examples 1 to 3 exhibit good activity in this test.

Example 9:

Action against *Spodoptera littoralis* and *Heliothis virescens* (larvae and eggs):

Three cotton plants each having a height of about 15–20 cm and grown in pots are treated with a sprayable liquid formulation of the test compound in a concentration of 800 ppm. After the spray coating has dried, the potted plants are placed in a metal container having a capacity of about 20 liters and covered with a glass plate. The humidity in the interior of the covered container is regulated such that no water of condensation forms. Direct light falling on the plants is avoided. The three plants are then infested altogether with:
- (a) 50 larvae of *Spodoptera littoralis* or *Heliothis virescens* in the $L_1$-stage;
- (b) 20 larvae of *Spodoptera littoralis* or *Heliothis virescens* in the $L_3$-stage;
- (c) 2 egg deposits of *Spodoptera littorali* or *Heliothis virescens*. (The procedure is that two leaves of each plant are put into a plexiglass cylinder sealed at both ends with muslin. Two egg deposits of Spodoptera, or a part of a cotton leaf with eggs of Heliothis deposited thereon, are added to the leaves sealed in the cylinder.)

Evaluation in comparison with untreated controls is made after 4 and 5 days, applying the following criteria:
- (a) the number of still living larvae,
- (b) inhibition of larval development and moulting,
- (c) feeding damage (shredding and perforation damage),
- (d) hatching rate (number of larvae hatched from the eggs).

In this test, the compounds of formula I according to Examples 1 to 3 exhibit good overall activity.

Example 10: Ovicidal action against *Spodoptera littoralis*

Eggs of *Spodoptera littoralis* deposited on filter paper are cut out of the paper and immersed in a solution of 800 ppm of the test compound in a 1:1 mixture of acetone-water. The treated deposits are then removed from this mixture and kept in plastic dishes at 28° C. and 60% humidity. The hatching rate, i.e. the number of larvae which have developed from the treated eggs, is determined after 5 days.

Compounds of formula I according to Examples 1 to 3 exhibit good activity in this test.

Example 11: Ovicidal action against *Laspeyresia pomonella* (eggs):

Egg deposits of *Laspeyrasia pomonella* not more than 24 hours old are immersed on filter paper for 1 minute in an aqueous acetonic solution containing 800 ppm of the test compound.

After the solution has dried, the eggs are placed in petri dishes and kept at a temperature of 28° C. The percentage of larvae hatched from the treated eggs is evaluated after 6 days.

Compounds of formula I according to Examples 1 to 3 exhibit good activity in this test.

Example 12: Action against *Anthonomus grandis* (adults)

Two cotton plants in the 6-leaf stage, in pots, are each sprayed with a wettable aqueous emulsion formulation containing 400 ppm of the test compound. After the spray coating has dried (about 1½ hours), each plant is populated with 10 adult beetles (*Anthonomus grandis*). Plastic cylinders, covered at the top with gauze, are then slipped over the treated plants populated with the test insects to prevent the beetles from migrating from the plants. The treated plants are then kept at 25° C. and about 60% relative humidity. Evaluation is made after 2, 3, 4 and 5 days to determine the percentage mortality of the beetles (percentage in dorsal position) as well as the anti-feeding action as compared with untreated controls.

Compounds of formula I according to Examples 1 to 3 exhibit good activity in this test.

Example 13:

Action against plant-destructive acarids: *Tetranychus urticae* (OP-sensitive) and *Tetranychus cinnabarinus* (OP-tolerant)

16 hours before the test for acaricidal action, the primary leaves of *Phaseolus vulgaris* plants are infected with an infested piece of leaf from a mass culture of *Tetranychus urticae* (OP-sensitive) and *Tetranychus cinnabarinus* (OP-tolerant). (The tolerance refers to the tolerance to diazinone). The treated infested plants are sprayed to drip point with a test solution containing the respective test compound in a concentration of 800 ppm. A count of the number of living and dead imagines and larvae (all mobile stages) is made under a stereoscopic microscope after 24 hours and again after 7 days. During the test run, the plants are kept in greenhouse compartments at 25° C.

The compounds of formula I according to Examples 1 to 3 exhibit good activity in this test.

Example 14: Insecticidal contact action against *Myzus persicae*

Pea plants which have been reared in water to a height of about 4 cm are each populated with about 200 insects of the species *Myzus persicae* before the start of the test. The treated plants are then sprayed to drip point 24 hours later with an aqueous suspension containing the test compound in a concentration of 800 ppm. A mortality count is made 48 hours after application. The test is carried out at 20°–22° C. and 60% relative humidity.

Compounds of formula I according to Examples 1 to 3 exhibit good activity in this test.

Example 15: Insecticidal contact action against *Aphis craccivora*

Before the start of the test, bean plants (*Vicia faba*) reared in pots are each populated with about 200 individuals of the species *Aphis craccivora*. The treated plants are sprayed 24 hours later to drip point with an aqueous formulation containing the test compound in a concentration 400 ppm. A mortality count is made after a further 24 hours.

Compounds of formula I according to Examples 1 to 3 exhibit good activity in this test.

Example 16: Action against *Laodelphax striatellus* and *Nilaparvata lugens* (nymphs)

The test is carried out with growing plants. The procedure is that 4 rice plants (thickness of stem c. 8 mm) about 20 cm in height are planted into each of a number of pots (diameter 8 cm). The plants in each pot are sprayed on a rotary table with 100 ml of an acetonic solution containing the test compound in a concentration of 400 ppm. After the spray coating has dried, each plant is populated with 20 nymphs of the test organisms in the third stage. To prevent the cicadas from escaping, a glass cylinder which is open at both ends is slipped over each of the plants and sealed with a gauze top. The nymphs are kept for 10 days on the treated plant until the next development stage has been reached. Percentage evaluation of mortality is made 1, 4 and 8 days after treatment.

Compounds of formula I according to Examples 1 to 3 exhibit good activity in this test.

Example 17: Action against soil insects (*Diabrotica balteata*) 350 ml of soil (consisting of 95 vol. % of sand and 5 vol. % of peat) are mixed with 150 ml of each of a number of aqueous emulsion formulations which contain the test compound in a concentration of 400 ppm. Plastic beakers with a diameter of about 10 cm at the top are then partly filled with the treated soil. Ten L$_3$-larvae of *Diabrotica balteata* are put into each beaker, then 4 maize seedlings are planted and the beaker is filled with soil. The beakers are sealed with plastic sheeting and kept at about 22° C. Ten days later the soil in the beakers is sieved and a mortality count of the remaining larvae is made. Compounds of formula I according to Examples 1 to 3 exhibit good activity in this test.

Example 18: Action against *Panonychus ulmi* (OP and carbamate resistant)

Potted apple seedlings with about 20 to 30 leaves are each populated with 60 adult females of *Panonychus ulmi*. The infested plants are sprayed after 7 days to drip point with an aqueous emulsion containing 400 ppm of the test compound. The treated plants are then stood in a greenhouse for a further 14 days at 25° C. and about 50% relative humidity.

After this time, evaluation is made by taking 20 leaves from each plant, removing the mite population from these leaves by means of a brushing device and counting the number of eggs, postembryonic stages and adults under a stereoscopic microscope. An assessment is made of the percentage reduction of the mite population as compared with untreated controls.

Compounds of formula I according to Examples 1 to 3 exhibit good activity in this test.

What is claimed is:

1. A compound of formula I

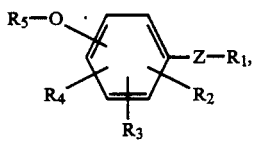
(I)

wherein
R$_1$ is C$_1$-C$_{12}$alkyl, C$_3$-C$_8$cycloalkyl, polycyclic alkyl containing a total of 7 to 10 carbon atoms, C$_1$-C$_{12}$alkyl which is substituted by 1 to 12 halogen atoms, C$_1$-C$_4$alkyl which is substituted by one or two C$_3$-C$_6$cycloaklyl radicals, alkoxyalkyl containing a total of 3 to 10 carbon atoms, C$_1$-C$_5$alkyl which is substituted by a phenyl radical, C$_1$-C$_5$alkyl which is substituted by a phenyl radical which is in turn substituted by one or two members selected from the group consisting of halogen, methyl, methoxy and ethoxy; or is C$_3$-C$_{10}$alkenyl or C$_3$-C$_{10}$alkynyl,
R$_2$ is hydrogen or C$_1$-C$_4$alkyl,
R$_3$ is C$_1$-C$_4$alkyl,
R$_4$ is hydrogen or C$_1$-C$_4$alkyl, and
R$_5$ is a radical selected from

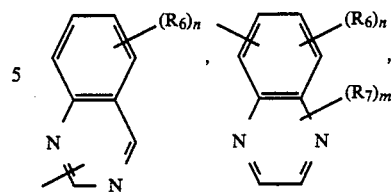

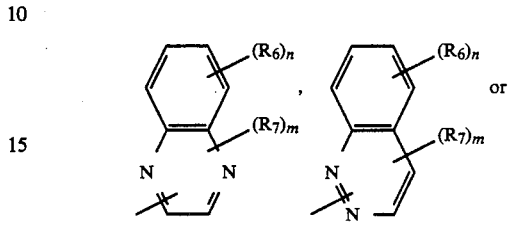

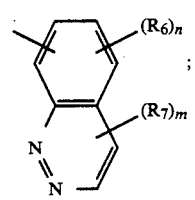

R$_6$ and R$_7$ are each independently of the other halogen, C$_1$-C$_4$alkyl, C$_1$C$_3$alkyl which is substituted by 1 to 7 halogen atoms, C$_1$-C$_4$alkoxy, C$_1$-C$_3$alkoxy which is substituted by 1 to 7 halogen atoms; or is phenyl,
R$_8$ is C$_1$-C$_4$alkyl,
R$_9$ is C$_1$-C$_4$alkyl or C$_3$-C$_4$alkenyl,
n is an integer from 0 to 3,
m is an integer from 0 to 2, and
Z is a group selected from

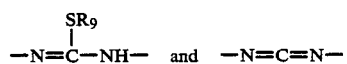

or a salt thereof.

2. A compound according to claim 1 of formula Ia

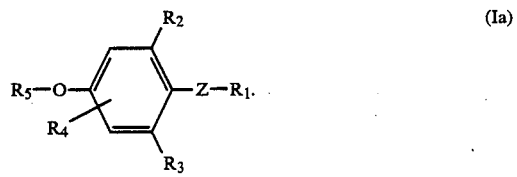
(Ia)

3. A compound according to claim 1, wherein R$_4$ is hydrogen.

4. A compound according to claim 1, wherein Z is

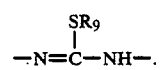

5. A compound according to claim 1, wherein Z is the group —N=C=N—.

6. A compound according to claim 1, wherein R$_5$ is the radical

and R₆ is halogen or trifluoromethyl.

7. A compound according to claim 1, wherein $R_1$ is $C_3$–$C_5$alkyl, $R_2$ and $R_3$ are each independently of the other $C_1$–$C_3$alkyl, and $R_9$ is methyl or ethyl.

8. A compound according to claim 1, wherein $R_1$ is isopropyl or tert-butyl, $R_2$ and $R_3$ are methyl or ethyl, $R_4$ is hydrogen, and $R_9$ is methyl.

9. A compound according to claim 1 of formula

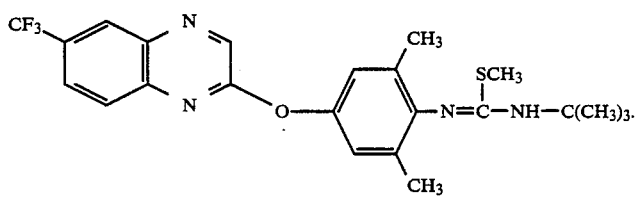

10. A compound according to claim 1 of formula

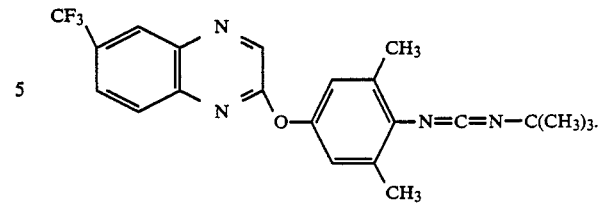

11. A pesticidal composition which contains, as active component, a compound of claim 1 together with a carrier or a other adjuvant.

12. A method of controlling insects or representatives of the order Acarina, which comprises treating said pests, their various development stages or the locus thereof, with a pesticidally effective amount of a compound of formula I according to claim 1 together with adjuvants and carriers suitable therefor.

13. A method of claim 12 for controlling insects and representatives of the order Acarina that are pests of animals and plants.

14. A method of claim 12 for controlling larval stages of plant-destructive insects.

15. A method of claim 12 for controlling plant-destructive mites and feeding insects.

* * * * *

UNITED STATES PATENT AND TRADEMARK OFFICE
CERTIFICATE OF CORRECTION

PATENT NO. : 4,963,550

DATED : 10/16/90

INVENTOR(S) : Manfred Boger et al

It is certified that error appears in the above-identified patent and that said Letters Patent is hereby corrected as shown below:

ON TITLE PAGE: item 62, second line should read:

--4,914,098--.

Signed and Sealed this

Eighteenth Day of August, 1992

*Attest:*

DOUGLAS B. COMER

*Attesting Officer*      *Acting Commissioner of Patents and Trademarks*